United States Patent [19]

Yamanaka

[11] Patent Number: 4,524,621
[45] Date of Patent: Jun. 25, 1985

[54] METHOD FOR MEASUREMENT OF VELOCITY OF SURFACE ACOUSTIC WAVE

[75] Inventor: Kazushi Yamanaka, Ibaraki, Japan

[73] Assignees: Agency of Industrial Science & Technology; Ministry of International Trade & Industry, both of Tokyo, Japan

[21] Appl. No.: 529,768

[22] Filed: Sep. 6, 1983

[51] Int. Cl.$^3$ ............................................. G01N 29/00
[52] U.S. Cl. ......................................... 73/597; 73/606
[58] Field of Search ................. 73/597, 606, 629, 642, 73/598

[56] References Cited

U.S. PATENT DOCUMENTS 4,459,852  7/1984  Chubachi et al. ..................... 73/606
4,462,256  7/1984  Moffett ................................. 73/642

OTHER PUBLICATIONS

R. D. Weglein, "A Model for Predicting Acoustic Material Signatures", *Applied Physics Letters*, vol. 34, No. 3, Feb. 1, 1979, pp. 179–181.

*Primary Examiner*—Stewart J. Levy
*Assistant Examiner*—John E. Chapman, Jr.
*Attorney, Agent, or Firm*—Oblon, Fisher, Spivak, McClelland & Maier

[57] ABSTRACT

The velocity of the surface acoustic wave of a test piece is determined by projecting an acoustic wave in the form of pulses through an acoustic lens onto the test piece thereby allowing the acoustic wave to form a focal point within the test piece, causing the projected acoustic wave to be separated into a component returned in consequence of specular reflection on the surface of the test piece, a component returned after having been propagated in the form of a leaky surface acoustic wave along the surface of the test piece, and a component returned in consequence of inner reflection on the boundary of the acoustic lens, measuring the intervals separating the times at which these three components are received at a common wave receiver, and calculating the velocity based on the time intervals thus found.

5 Claims, 2 Drawing Figures

METHOD FOR MEASUREMENT OF VELOCITY OF SURFACE ACOUSTIC WAVE

BACKGROUND OF THE INVENTION

1. Field of the Invention

This invention relates to a method for the measurement of the velocity of the surface acoustic wave generated on a test piece when an acoustic wave is projected thereon.

2. Description of the Prior Art

A method of inspecting a test piece for inner defects by injecting an acoustic wave into the test piece has been known to the art.

The acoustic lens which is employed in acoustic microscopy, for example, has been known to possess an ability to excite and detect leaky surface acoustic waves. Recently, a method of making use of this ability of the acoustic lens in effecting the measurement of the velocity of the surface acoustic wave which is generated on a test piece when the test piece is irradiated with an acoustic wave has been reported. This method is based on the principle that when the acoustic lens is moved in a perpendicular direction relative to the surface of the test piece and the amplitude V of the reflected wave is measured as the function of the distance z between the surface of the test piece and the focal point of the lens, the velocity of the surface acoustic wave of the test piece can be determined from the minimal cyclic interval Δz appearing in the V(z) curve obtained. Since this method is capable of accurately measuring the elastic property of a solid surface in a microscopic area on the order of 1 to 100 microns, it is attracting mounting interest as a new nondestructive testing method advantageously applicable to tools, mechanical parts, and electronic components which have undergone coating with PVD, CVD, etc. surface hardening, carburizing and other surface treatments.

The measurement of the velocity of the surface acoustic wave by the method described above, however, inevitably entails an operation of mechanically moving the acoustic lens in a perpendicular direction relative to the surface of the test piece with the aid of a micrometer, for example. The measurement of the velocity at one point on the test piece requires at least several seconds. Besides, the mechanical accuracy of this measurement poses a problem. When the measurement of velocity is made at a multiplicity of points on the surface of a test piece to find the distribution of velocity on the surface or when real-time measurement is performed on a test piece whose surface condition varies from moment to moment, this method poses a problem with respect to the speed with which the measurement operation can be carried out.

SUMMARY OF THE INVENTION

An object of this invention is to provide a method which permits the velocity of a surface acoustic wave of a test piece to be rapidly and accurately determined merely through processing of electric signals without requiring any mechanical movement of the acoustic lens.

To be specific, the method of this invention determines the velocity of the surface acoustic wave of a test piece by projecting an acoustic wave in the form of pulses through an acoustic lens onto the test piece so that the acoustic wave may converge to a focal point located inside the test piece, detecting the intervals separating the times at which the component of the acoustic wave returned on account of specular reflection on the surface of the test piece, the component thereof returned after propagation in the form of leaky surface acoustic wave through the surface layer of the test piece, and the component thereof returned on account of internal reflection inside the acoustic lens are respectively received, and calculating the velocity on the basis of the the intervals so detected.

The other objects and the other characteristics of this invention will become apparent to those skilled in the art as the following disclosure of a preferred embodiment is made with reference to the accompanying drawings.

DESCRIPTION OF THE PREFERRED EMBODIMENT

Figure 1:
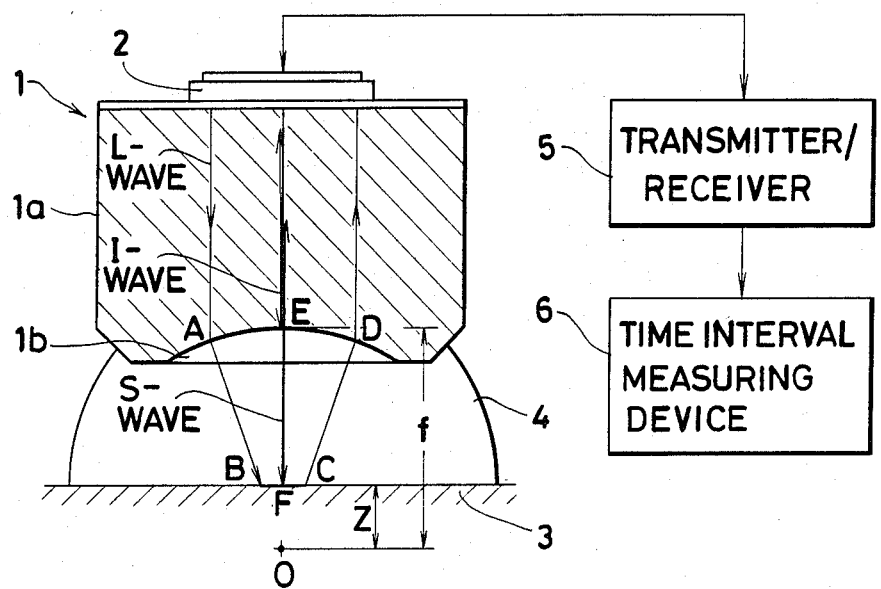
FIG. 1 is a schematic structural diagram illustrating a typical device to be used for working the method of this invention.

Referring to FIG. 1, 1 denotes an acoustic lens similar to the acoustic lens used in acoustic microscopy and comprises a tubular part 1a formed of a single crystal of alumina or fused quartz and a depression 1b of concave surface formed in the leading terminal surface of the tubular part 1a. On the acoustic lens 1, a piezoelectric transducer 2 is disposed so that the vertical wave generated by the piezoelectric transducer 2, when refracted by the concave surface of the depression 1b opposed to a test piece 3, will converge to the focal point O located within the test piece 3. A wave transmitter/receiver 5 connected to the piezoelectric transducer 2 serves the dual purpose of generating an acoustic wave in the form of pulses of short duration and receiving reflected waves through the piezoelectric transducer 2. To this wave transmitter/receiver 5 is connected a time interval measuring device 6 which serves the purpose of measuring the intervals between the times at which the different reflected waves described afterward are received by the wave transmitter/receiver 5. Between the leading terminal surface of the acoustic lens 1 and the test piece 3, there is interposed a coupler 4 of water or alcohol for the purpose of ensuring sure propagation of the acoustic wave between the acoustic lens 1 and the test piece 3.

In the measuring device of such a construction as described above, when the acoustic wave in the form of pulses generated by the wave transmitter/receiver 5 and projected through the acoustic lens 1 onto the test piece 3, it is preponderantly divided into the following three components.

First, there is the component of the acoustic wave which passes through the center of the acoustic lens 1, advances straight from the point "E" of the lens 1 through the water or other liquid which is used as the coupler 4 and, on reaching the point "F" on the surface of the test piece 3, is caused to advance backwardly in consequence of specular reflection, thus completing the path of $\overline{EFE}$ (hereinafter referred to as "S-wave"). Then, there is the component of the acoustic wave which passes through the acoustic lens 1 at a distance from the center of the lens, is refracted at the point "A" in the concave surface of the depression 1b, advances through the coupler 4 and arrives at the point "B" on the surface of the test piece 3 at a distance from the center point "F", there to be converted into the surface acoustic wave which propagates parallell to the surface of the test piece and only in the neighborhood of the surface of the test piece, and thus advances from the point "B" through the point "F" to the point "C" and, on reaching the point "C", passes into the coupler 4 again and then into the lens 1 through the point "D" on the concave surface of the depression 1b, and finally returns to the transducer 2. This is the leaky surface acoustic wave (hereinafter referred to as "L-wave"). This invention is aimed at determining the velocity at which the L-wave is propagated in the form of a surface acoustic wave along the path $\overline{BFC}$ on the surface of the test piece. This velocity carries information concerning any defect in the neighborhood of the surface of the test piece and concerning any change in the test piece due to surface treatment.

There is also the component of the acoustic wave which is internally reflected at the point "E" of the acoustic lens 1. This is the internally reflected wave (hereinafter referred to as "I-wave").

Figure 2:
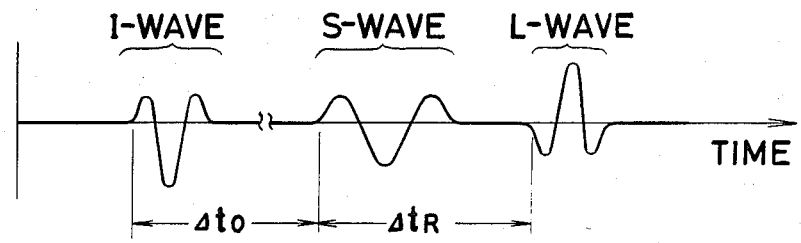
FIG. 2 is a graph showing the time relation between the different reflected waves involved in the method of this invention.

FIG. 2 illustrates the relation of the times at which the aforementioned S-wave, L-wave, and I-wave are returned to the piezoelectric transducer 2. The I-wave is the first to return to the transducer 2, followed by the S-wave and the L-wave. Thus, these components of the acoustic wave are returned in clearly discrete waves.

Let $\Delta t_O$ stand for the interval between the times at which the I-wave and the S-wave reach the piezoelectric transducer 2 and $\Delta t_R$ for the interval between the times at which the S-wave and the L-wave reach the piezoelectric transducer 2, then they will satisfy the equations of the following formulas (1) and (2). In these formulas, f stands for the focal distance of the lens 1, $v_O$ for the velocity of the acoustic wave in the liquid used as the coupler 4, and $v_R$ for the velocity of the leaky surface acoustic wave on the test piece.

$$\Delta t_O = 2(f - z)/v_O \quad (1)$$

$$\Delta t_R = \frac{2z}{v_O}(1 - \sqrt{1 - v_O^2/v_R^2}) \quad (2)$$

Here, the distance z between the surface of the test piece and the focal point of the lens is variable with the degree of irregularity of the surface of the test piece. When the surface irregularity of a test piece is unknown, therefore, the velocity $v_R$ cannot be calculated from the time interval $\Delta t_R$ in accordance with the aforementioned formula (2). In this case, the equation of the following formula (3) which no longer contains the unknown distance "z" is derived by substituting the formula (1) in the formula (2).

$$v_R = \left[ \frac{\Delta t_R}{v_O(f - v_O\Delta t_O/2)} - \frac{\Delta t_R^2}{4(f - v_O\Delta t_O/2)^2} \right]^{-\frac{1}{2}} \quad (3)$$

This formula (3) shows that the velocity of the surface acoustic wave propagated on the surface of a test piece can be calculated based on the time interval $\Delta t_O$ between the I-wave and the S-wave and the time interval $\Delta t_R$ between the S-wave and the L-wave which are both measured by the time interval measuring device 6 without reference to the surface irregularity of the test piece.

The acoustic wave to be advantageously employed for practical embodiment of this invention has a frequency in the range of about 1 to 1000 MHz, preferably from 10 to 100 MHz. This acoustic wave is transmitted in the form of pulses to the acoustic lens. The adoption of this particular form of pulses is for the sake of ensuring clear discretion of the I-wave, the S-wave, and the L-wave along the course of time. The width of the pulses must be small enough to warrant perfect separation of the three waves mentioned above. The width of the pulse is generally required to be less than a value of about 100 ns, which is variable with the size of the lens and the velocity of the surface acoustic wave on the test piece.

The acoustic lens is made of a single crystal of alumina or fused quartz and has a diameter in the range of about 10 to 40 mm and a thickness in the range of about 5 to 30 mm and a focal distance in the range of about 0.5 to 5 mm. The depth of the focal point which the acoustic lens forms in the test piece is about 10 to 90% of the focal distance mentioned above. The distance travelled by the surface acoustic wave, the area of the zone for effective measurement, and the accuracy of measurement all increase and the positional resolvability alone decreases in proportion as the depth of the focal point increases.

Concrete examples of the test piece on which the measurement by the method of this invention can be effectively performed include various articles made of metals, ceramics, polymeric materials, and their composite materials. In fact, any material can be given effective measurement by the method of this invention insofar as the dependency of the velocity of the acoustic wave upon the frequency and the attenuation of the acoustic wave are small and consequently the waveform of the L-wave is not appreciably different from the waveform of the excited wave.

The wave transmitter/receiver 5 to be used for the purpose of this invention is required to be capable of transmitting, receiving, and amplifying electric pulses having a pulse width in the range of about 1 to 100 ns and a peak power in the range of about 0.1 to 10 W. Any wave transmitter/receiver which is usually employed as an supersonic flaw detector, therefore, may be used effectively.

The time interval measuring device 6 which functions to calculate the time intervals, $\Delta t_O$ and $\Delta t_R$, by processing the signals from the wave transmitter/receiver 5 is either of the type adapted to detect the times at which the I-wave, the S-wave, and the L-wave begin to rise and calculate the intervals intervening between these times or of the type adapted to detect the times at which the respective pulses reach their peaks and find the intervals intervening between these times. In the case of the latter type, since the path for the propagation of the S-wave has a certain distribution and consequently the S-wave possesses a broader waveform than the I-wave or the L-wave as illustrated in FIG. 2, the device 6 must be adapted automatically to effect deduction of the compensation constant $t_c$ from the peak time of the S-wave. On the other hand, this type is less liable to the influence of the change in the amplitude of the L-wave and proves to be advantageous over the type which relies on the times at which the waves begin to rise.

As regards the configuration of this device, a hardware version may reside in combining a voltage comparator with a counter circuit and a software version may comprise subjecting waveforms of pulses to A/D conversion and performing necessary arithmetic operations on the outcomes of the A/D conversion with the aid of a computer.

In the method of measurement contemplated by this invention as described above, the measurement of the time intervals can be effected only through processing of electric signals without entailing any mechanical movement of the acoustic lens or any other part of the device. Thus, this method provides very rapid and highly accurate measurement of the velocity of the acoustic wave propagated on the surface of a test piece. For example, it permits the elastic property and other related properties of the surface layer of a tool or machine part which faithfully reflect hardness and wear resistance thereof to be determined on a real-time basis without requiring any destruction of the test piece. Thus, the present invention will make a great economic contribution to the industry.

When the measurement of the velocity of the surface acoustic wave is required to be performed at a specific site on the test piece 3, the acoustic lens 1 need not be moved as in the axial direction thereof. When the measurement of the velocity $v_R$ is required to be made at a multiplicity of sites on the test piece to determine the distribution of velocity, for example, the method of this invention can be carried out by incorporation of proper means capable of two-dimensionally scanning the surface of a test piece to obtain information on the entire surface of the test piece with ease.

Now, one example of this invention will be described below.

In an apparatus constructed as illustrated in FIG. 1, a PVDF film 30 μm in thickness was used as a broadband piezoelectric transducer and a lens made of fused quartz and having a diameter of 25 mm, a thickness of 20 mm, and a focal distance of 4 mm was used as an acoustic lens. The transducer and the acoustic lens were set up so that the lens would form a focal point at a depth of 1.5 mm in a test piece (z=1.5 mm). Water was used as a coupler, which had a velocity of 1486 m/s.

To the aforementioned acoustic lens an acoustic wave pulse of a frequency spectrum in the range of 10 to 50 MHz was fed at a pulse width of 30 ns. The measurement of the time intervals separating the S-wave, the I-wave, and the L-wave was effected by a time interval measuring device detecting the times at which the pulses of these waves reached their peaks, deducting from the peak time of the S-wave the compensation constant $t_c$ of the value of 24 ns selected to eliminate the discrepancy between the measured velocity on fused quartz and the velocity reported in the literature, and calculating the intervals intervening between the peak positions. The same value of $t_c$ was used for all test pieces regardless of the dissimilar materials involved.

The measurement was performed on SKD 11 steel, soda glass, Si (111) surface, and sapphire (0001) surface. The results of the measurement are compared with the values of velocities $v_R$ reported in the literature, and the values found by some other method in the following table.

TABLE

| Material tested | Velocity reported in literature (km/s) | Time interval, $\Delta t_R$ (ns) | Time interval $\Delta t_O$ (ns) | Velocity found (km/s) | Error (%) |
|---|---|---|---|---|---|
| SKD 11 steel | 2.950 | 265 | 3370 | 3.00 | +1.69 |
| Soda glass | 3.145 | 240 | 3370 | 3.14 | −0.095 |
| Si (111) surface | 4.645 | 110 | 3370 | 4.56 | −1.87 |
| Sapphire (0001) surface | 5.630 | 70 | 3370 | 5.69 | +0.98 |

From the table given above, it is noted that the method according to the present invention was capable of measuring velocities in the range of from 2950 m/s to 5630 m/s accurately to within ±2%.

What is claimed is:

1. A method for the measurement of the velocity of the surface acoustic wave of a test piece, which comprises disposing an acoustic lens to have its focal point located within said test piece, projecting an acoustic wave in the form of pulses onto said test piece through said acoustic lens, measuring the interval separating the time at which a first component of the projected acoustic wave is returned in consequence of specular reflection on the surface of said test piece and the time at which a second component of the projected acoustic wave is returned after having been propagated in the form of a leaky surface acoustic wave along the surface of said test piece, measuring the interval separating said time of said first component and the time at which a third component of the projected acoustic wave is returned in consequence of internal reflection on the boundary of said acoustic lens, and calculating the velocity of the surface acoustic wave of said test piece based on the two time intervals obtained.

2. A method according to claim 1, further comprising interposing a coupler between the surface of said acoustic lens opposed to said test piece and said test piece.

3. A method according to claim 2, wherein said coupler is water.

4. A method according to claim 1, wherein said acoustic wave has a frequency spectrum in the range of 10 to 100 MHz.

5. A method according to claim 1, wherein said acoustic wave has a pulse width of less than about 100 ns.

* * * * *